US008771992B2

(12) United States Patent
Trilli et al.

(10) Patent No.: US 8,771,992 B2
(45) Date of Patent: Jul. 8, 2014

(54) BIOTECHNOLOGICAL PRODUCTION OF CHONDROITIN

(71) Applicant: Gnosis S.p.A., Milan (IT)

(72) Inventors: Antonio Trilli, Magliasco (CH); Immacolata Busiello, Giubiasco (CH); Simona Daly, Monza (IT); Francesca Bagatin, Rovello Porro (IT)

(73) Assignee: GNOSIS S.p.A., Milan (IT)

( * ) Notice: Subject to any disclaimer, the term of this patent is extended or adjusted under 35 U.S.C. 154(b) by 0 days.

(21) Appl. No.: 14/078,809

(22) Filed: Nov. 13, 2013

(65) Prior Publication Data

US 2014/0073772 A1    Mar. 13, 2014

Related U.S. Application Data

(62) Division of application No. 13/168,289, filed on Jun. 24, 2011, now Pat. No. 8,609,394.

(30) Foreign Application Priority Data

Jul. 9, 2010   (IT) ............................... MI2010A1264
Jul. 15, 2010  (IT) ............................... MI2010A1300

(51) Int. Cl.
  *C12P 19/26*   (2006.01)
  *C12P 19/28*   (2006.01)
  *C12Q 1/68*    (2006.01)

(52) U.S. Cl.
  USPC ................................. 435/84; 435/85; 435/6.1

(58) Field of Classification Search
  USPC .................................................. 435/6, 84, 85
  See application file for complete search history.

(56) References Cited

U.S. PATENT DOCUMENTS

| 2007/0281342 | A1 | 12/2007 | DeAngelis |
| 2009/0263867 | A1 | 10/2009 | Sugiura et al. |
| 2011/0244520 | A1 | 10/2011 | Doherty et al. |

FOREIGN PATENT DOCUMENTS

| WO | 2008133350 | | 11/2008 |
| WO | 2011109438 | A1 | 9/2011 |

OTHER PUBLICATIONS

Certificate of Deposit and Viability for Accession No. DSM 23578, Deutsche Sammlung von Mikroorganismen und Zellkulturen GmbH, May 5, 2010.
Certificate of Deposit and Viability for Accession No. DSM 23644, Deutsche Sammlung von Mikroorganismen und Zellkulturen GmbH, Jun. 1, 2010.
EPO Search Report from Italian priority Application No. IT MI20101300, Feb. 14, 2011.
EPO Search Report from Italian priority Application No. IT MI20101264, Feb. 14, 2011.
Volpi, Nicola, Chondroitin C Lyase [4.2.2.] is Unable to Cleave Fructosylated Sequences Inside the Partially Fructosylated *Escherichia coli* K4 Polymer, Glycoconj J, 2008, pp. 451-457, vol. 25, Springer Science + Business Media, LLC.
Ninomiya, Toshio, et al., Molecular Cloning and Characterization of Chondroitin Polymerase from *Escherichia coli* Strain K4, The Journal of Biological Chemistry, 2002, pp. 21567-21575, vol. 277, Issue 24, The American Society for Biochemistry and Molecular Biology, Inc.
Lidholt, Kerstin, et al., Biosynthesis of the *Escherichia coli* K4 Capsule Polysaccharide, The Journal of Biological Chemistry, 1997, pp. 2682-2687, vol. 272, Issue 5, The American Society for Biochemistry and Molecular Biology, Inc.
McNally, David J., et al., The HS:1 Serostrain of *Campylobacter jejuni* has a Complex Teichoic Acid-Like Capsular Polysaccharide with Nonstoichiometric Fructofuranose Branches and O-Methyl Phosphoramidate Groups, The FEBS Journal, 2005, pp. 4407-4422, vol. 272, Institute for Biological Sciences, National Research Council of Canada, Ottawa, Ontario, Canada.
Volpi, Nicola, Separation of Capsular Polysaccharide K4 and Defructosylated K4 by High-Performance Capillary Electrophoresis, Electrophoresis, 2004, pp. 692-696, vol. 25, Wiley-VCH Verlag GmbH & Co., Weinheim, Germany.
Branefors-Helander, Paula, et al., Structural Studies of Two Capsular Polysaccharides Elaborated by Different Strains of *Haemophilus influenzae* Type e, Carbohydrate Research, 1981, pp. 77-84, vol. 88, Elsevier Scientific Publishing Company, Amsterdam, The Netherlands.
Raungsomboon, Suneerat, et al., Production, Composition, and Pb2+ Adsorption Characteristics of Capsular Polysaccharides Extracted from a Cyanobacterium Gloeocapsa gelatinosa, Water Research, 2006, pp. 3759-3766, vol. 40, Elsevier Ltd.
Knirel, Yuriy A., et al., Structural Studies on the Short-Chain Lipopolysaccharide of Vibrio Cholerae O139 Bengal, Eur. J. Biochem., 1997, pp. 402-410, vol. 247, FEBS.
Rodriguez, Maria-Luisa, et al., Structure and Serological Characteristics of the Capsular K4 Antigen of *Escherichia coli* O5:K4:H4, a Fructose-Containing Polysaccharide with a Chondroitin Backbone, Eur. J. Biochem., 1988, pp. 117-124, vol. 177, FEBS.
International Search Report and Written Opinion of the International Searching Authority for corresponding International Application No. PCT/EP2011/059069, Aug. 11, 2011.

*Primary Examiner* — Maryam Monshipouri
(74) *Attorney, Agent, or Firm* — Amin Talati, LLC; Janine A. Moderson; George M. Carrera, Jr.

(57) ABSTRACT

Chondroitin is produced by culturing a recombinant microorganism which is obtained by inactivation of a gene encoding an enzyme responsible for addition of fructose residues to the linear chondroitin polysaccharide in a microorganism producing a fructosylated derivative of chondroitin.

10 Claims, 4 Drawing Sheets

BIOTECHNOLOGICAL PRODUCTION OF CHONDROITIN

This application is a Divisional of U.S. application Ser. No. 13/168,289, filed Jun. 24, 2011, now U.S. Pat. No. 8,609,934, which claims priority to Italian Patent Application No. MI2010A001300, filed Jul. 15, 2000, and Italian Patent Application No. MI2010A001264, filed Jul. 9, 2010. The entire disclosures of each of the foregoing patent applications are hereby incorporated by reference.

SEQUENCE LISTING

The Sequence Listing is submitted as an ASCII text file in the form of a file named G71597_SEQUENCE_LISTING.txt (12,345 bytes) created on May 31, 2011, which is herein incorporated by reference in its entirety.

FIELD OF THE INVENTION

The present invention relates to a novel recombinant microorganism producing chondroitin and a method for the biotechnological production of chondroitin.

In the present invention the term chondroitin indicates a linear polysaccharide defined as a linear glycosaminoglycan constituted by alternating residues of D-glucuronic acid (GlcUA) and N-acetyl-D-galactosamine (GalNAc) bound by $\beta$1-3 (GlcUA→GalNAc) and $\beta$1-4 (GalNAc→GlcUA) bonds.

BACKGROUND OF THE INVENTION

Chondroitin sulphate is a glycosaminoglycan in which glucuronic acid (GlcUA) and an N-acetyl-D-galactosamine (GalNAc) are linearly and alternatively bound by $\beta$1-3 linkage and $\beta$1-4 linkage respectively to form a linear polysaccharide chain that is sulphated to varying degrees in its GalNAc residues.

It is present in animals, in cartilages and connective tissue, playing an important role in cell adhesion, tissue regeneration, nerve extension and the like.

The production of chondroitin from non-animal sources is an important and desirable step towards the production of non-animal-derived chondroitin sulphate.

The available patent literature describes several methods for the production of non-animal-derived chondroitin.

In addition, several chondroitin synthase genes, derived from both animals and microorganisms, have been cloned and sequenced.

A method for producing chondroitin has been provided by using a recombinant Gram-positive *Bacillus* bacterium introduced with a chondroitin synthase gene derived from *Pasteurella multocida* (US 2007/0281342 A1).

A further invention describes a method for producing chondroitin by introducing both the kfoC and kfoA genes, derived from *Escherichia coli* O5:K4:H4, into a UDP-glucuronic acid-producing bacterium (WO2008/133350).

Another invention describes an in vitro chondroitin synthesis in an enzymatic system comprising both the *Escherichia coli* O5:K4:H4 chondroitin synthase and the precursors of reaction (US2009/0263867 A1).

It is known that *Escherichia coli* O5:K4:H4 is able to produce a capsular polysaccharide (the K4 polysaccharide) having the same backbone structure as that of chondroitin, to which fructose residues are linked to the GlcUA residues (see, e.g., N. Volpi, *Glycoconj. J.*, 25:451-457 (2008)). Therefore, the K4 polysaccharide consists of a repeating trisaccharide unit comprising a D-glucuronic acid (GlcUA) moiety and an N-acetyl-D-galactosamine (GalNAc) moiety linked by a $\beta$1-3 (GlcUA→GalNAc) and a fructose residue bound to the C3-hydroxyl group of the GlcUA residue. The fructose residues thus constitute branches of the resulting linear polysaccharide.

Removal of the fructose residues has been achieved by hydrolytic treatment in acid conditions (N. Volpi, *Electrophoresis*, 25, 692-696 (2004)).

Although both the *Escherichia coli* O5:K4:H4 capsule antigen gene cluster and the metabolic pathways leading to the sugars constituting the K4 linear polysaccharide have been extensively studied, the glycosyl-transferase activity responsible for the addition of the fructose moieties to the linear polysaccharide to give the K4 polysaccharide, has so far not been identified.

The novel feature of the present invention is the direct production of high-molecular weight chondroitin by a recombinant microorganism obtained by inactivating a gene encoding an enzyme responsible for the addition of fructose residues to the chondroitin back-bone thus obviating the need to submit the K4 polysaccharide to the hydrolytic removal of the fructose residues bound to the GlcUA moieties to obtain chondroitin.

BRIEF SUMMARY

According to one aspect, a recombinant microorganism producing chondroitin is provided characterized in that said microorganism is obtained by subjecting a gene originally present therein, which encodes a protein responsible for the addition of fructose residues to the linear chondroitin backbone, to inactivation, said inactivation including deletion or substitution entirely or part of said gene or disruption by insertion of an additional nucleotide sequence.

In another aspect, a method for the biotechnological production of chondroitin includes culturing in a suitable medium the recombinant microorganism, and recovering the chondroitin produced from its broth culture. Any recombinant microorganism capable of producing chondroitin obtained according to the method described above to inactivate a gene encoding an enzyme responsible of fructose residues addition to chondroitin may be used in the culturing step.

Other objects and advantages will be apparent to those skilled in the art from the following detailed description taken in conjunction with the examples and the appended claims.

DETAILED DESCRIPTION

An object of the present invention is to provide a recombinant microorganism producing chondroitin, defined as a linear glycosaminoglycan consisting of alternating residues of D-glucuronic acid (GlcUA) and N-acetyl-D-galactosamine (GalNAc) bound by $\beta$1-3 linkage and $\beta$1-4 linkage respectively, characterized in that in said microorganism a gene encoding an enzyme responsible for the addition of fructose residues to the chondroitin back-bone is inactivated.

Therefore, according to an aspect of this invention a recombinant microorganism is provided producing chondroitin characterized in that said microorganism is obtained by subjecting a gene originally present therein, which encodes a protein responsible for the addition of fructose residues to the linear chondroitin back-bone, to inactivation, said inactivation including deletion or substitution entirely or part of said gene or disruption by insertion of an additional nucleotide sequence.

According to a preferred aspect of this invention, the recombinant microorganism of the present invention obtained by inactivation of the gene encoding a protein having a fructosyl-transferase activity is derived from a bacterium that belongs to the species *Escherichia coli*, and preferably belongs to the group 2 of the K antigens that includes well-known serotypes such as K1, K5, K7, K12.

Although according to a representative embodiment of this invention, the recombinant microorganism having the ability to produce chondroitin is derived from *Escherichia coli* O5:K4:H4, any of the microorganisms belonging to the K antigen group, irrespective of whether they share any gene homology with *Escherichia coli* O5:K4:H4, can be employed. Examples of said microorganisms include bacteria belonging to the genera *Haemophilus* such as *H. influenzae* (Branefors-Helander P., et al., *Carbohydr. Res., Vol.* 88, Jan. 15, 1981), *Campylobacter* such as *C. jejuni* (McNally D J, Jarrell H C, Li J, Khieu N H, Vinogradov E, Szymanski C M, Brisson J R., *FEBS J.*, Vol. 272, No 17, 4407-4422, September 2005), *Gloeocapsa* such as *G. gelatinosa* (Raungsomboon S, Chidthaisong A, Bunnag B, Inthorn D, Harvey N W., *Water Res.*, Vol. 40, No 20, 3759-3766, December 2006) and *Vibrio* such as *V. cholerae* (Knirel Y A, Widmalm G, Senchenkova S N, Jansson P E, Weintraub A, *Eur. J. Biochem*, Vol. 247, 402-410, July 1997).

More preferably, the bacterium from which the recombinant microorganism of this invention producing chondroitin is derived is *Escherichia coli* serotype O5:K4:H4, which contains the kfoE gene, encoding a protein having a fructosyl-transferase activity.

The kfoE gene is known to be located within the *E. coli* K4 antigen gene cluster (GenBank AB079602) that contains genes found by the inventors to possess a significant homology with genes from other microorganisms, which are likely to be involved in bacterial capsule production (T. Ninomiya, N. Sugiura, A. Tawada, K. Sugimoto, H. Watanabe and K. Kimata, *J. Biol. Chem.*, Vol. 277, No 24, 21567-75, Jun. 14, 2002).

The bacterium most preferably used to obtain the recombinant microorganism of the present invention is *Escherichia coli* O5:K4:H4, strain U1-41, available from ATCC (American Type Culture Collection, Manassas, Va., US) under the accession number ATCC23502.

According to a representative embodiment of this invention the recombinant microorganism is a microorganism producing chondroitin wherein the gene subjected to inactivation is a gene coding for a protein selected from the group consisting of the following (A), (B), and (C):

(A) a protein comprising the amino acid sequence of SEQ ID No 2;

(B) a protein comprising the amino acid sequence of SEQ ID No 2 modified by deletion, substitution, or insertion of one or more amino acids, and having a fructosyl-transferase activity; and (C) a protein comprising an amino acid sequence having homology of at least 50% with the amino acid sequence of SEQ ID No 2 and having a fructosyl-transferase activity.

The microorganism according to this invention is a microorganism wherein the inactivated gene is the kfoE gene or a DNA selected from the group consisting of the following (a), (b), and (c):

(a) a DNA comprising the nucleotide sequence of SEQ ID No 1;

(b) a DNA that hybridizes with a DNA comprising the nucleotide sequence complementary to SEQ ID No 1 and encodes a protein having a fructosyl-transferase activity; and (c) a DNA comprising a nucleotide sequence having a homology of at least 50% with the nucleotide sequence of SEQ ID No 1 and encoding a protein having a fructosyl-transferase activity.

An object of the present invention is a microorganism producing chondroitin wherein kfoE inactivation is obtained by modification of its nucleotide sequence, such as by deleting or substituting, entirely or in part, the nucleotide sequence described under (a), (b) or (c) above.

Another object of the present invention is a microorganism wherein kfoE inactivation is obtained by inserting, one or more nucleotides, into the nucleotide sequence described under (a), (b) or (c) above.

According to a most preferred aspect of this invention, the recombinant derivative of *Escherichia coli* O5:K4:H4 strain U1-41 (from now on referred to as *E. coli* K4) is obtained by inactivation of the kfoE gene, encoding a putative fructosyl-transferase, by means of nucleotide deletion.

The present invention discloses how the disruption of the kfoE gene leads to the direct production of the K4 polysaccharide lacking the fructose residues, i.e., of chondroitin.

According to a further preferred aspect of this invention, the recombinant *E. coli* K4 of the present invention is obtained by using a method to disrupt chromosomal genes in which PCR primers provide the homology to the targeted gene (Datsenko and Wanner, *PNAS*, Vol. 97, No 12, 6640-6645, Jun. 6, 2000).

The recombinant *E. coli* K4 strain of the present invention has been subjected to the inactivation of the chromosomal kfoE gene first by substituting most of its nucleotide sequence with an exogenous kanamycin resistance gene ("first genetic modification") and then by deleting the inserted gene using a FLP recombinase expression vector ("second genetic modification").

The recombinant *E. coli* K4 strain obtained after the first genetic modification, referred to as *E. coli* K4 (ΔkfoE/kan$^R$) has been deposited on Apr. 30, 2010 at the Deutsche Sammlung von Mikroorganismen und Zellkulturen GmbH, Inhoffenstrasse 7B, 38124 Braunschweig, Germany, according to the Budapest Treaty, under the accession number DSM23578.

The recombinant *E. coli* K4 strain obtained after the second genetic modification, referred to as *E. coli* K4 (ΔkfoE) has been deposited on May 26, 2010 at the Deutsche Sammlung von Mikroorganismen und Zellkulturen GmbH, Inhoffenstrasse 7B, 38124 Braunschweig, Germany, according to the Budapest Treaty, under the accession number DSM23644.

The inactivation of the kfoE gene was achieved by means of 3 successive bacterial transformations firstly with the Red Recombinase expression plasmid (pKD46), secondly with a DNA fragment derived from a template plasmid (pDK4) suitably modified to provide homology with the kfoE gene, and thirdly with the helper plasmid expressing the enzyme FLP recombinase (pCP20).

In order to obtain the first genetic modification of *E. coli* K4, both the pKD46 plasmid (GenBank: AY048746) and the linear DNA fragment have been used.

The pKD46 plasmid, used in the first step of *E. coli* K4 transformation, consists of 2154 nucleotides from phage lambda and of the gene encoding resistance to ampicillin. This plasmid promotes an enhanced rate of recombination when using linear DNA fragments.

The linear DNA fragment used in the subsequent transformation of *E. coli* K4 has been obtained by PCR using several pairs of primers that include homology extensions to both the kfoE gene and the template plasmid pKD4 carrying a kanamycin resistance cassette (GenBank: AY 048743).

This procedure was able to generate a linear DNA fragment carrying a kanamycin resistance cassette, having the kfoE 5' and 3' homologous termini at its ends.

In one embodiment of this invention, bacterial transformation was effected by electroporation that was selected due to its ability to generate easily double transformants that could be recovered from plates containing both ampicillin and kanamycin.

However, although electroporation is the preferred technique, this result could be achieved by any known transformation method such as calcium chloride transformation or dextran-DEAE transformation.

With the aim to verify the correct location of the substitution of the original DNA sequence with the kanamycin resistance cassette in the transformants of *E. coli* K4 (ΔkfoE/$kan^R$), several PCR amplifications have been performed, using 2 nearby locus-specific primers pairs: the first primers pair was able to demonstrate the formation of a new junction between kfoE remaining 5' terminus and the inserted kan gene, while the second primer pair was able to demonstrate the formation of a new junction between the inserted kan gene and kfoE remaining 3' terminus.

The helper plasmid used to remove the kanamycin resistance cassette ("second genetic modification") was plasmid pCP20, carrying the yeast FLP recombinase gene and an ampicillin resistance gene. Both pKD46 and pCP20 plasmids are temperature-sensitive vectors that were subsequently removed from transformant strains of *E. coli* K4 following growth at 43° C.

A sequencing analysis has been performed on *E. coli* K4 (ΔkfoE/$kan^R$) to confirm the substitution of the kfoE gene, wholly or in part, with the kanamycin resistance cassette. Likewise, a sequencing analysis has been performed on *E. coli* K4 (ΔkfoE) to verify the subsequent deletion of the kanamycin resistance cassette, resulting in the final production of the kfoE-disrupted bacterial strain.

The method used for the successful construction of a recombinant *E. coli* K4 capable of producing a non-glycosylated variant of a natural glycosaminoglycan is of general applicability and can be advantageously applied to other glycosylated products where it is desirable to prevent such glycosylation. In conclusion, a general method was developed for obtaining microorganisms capable of producing non-glycosylated variants of natural glycosaminoglycans.

Another object of the present invention is to provide a method for the biotechnological production of chondroitin comprising the following steps:
(1) culturing in a suitable medium a recombinant microorganism; and
(2) recovering the chondroitin produced from its broth culture.

Any recombinant microorganism capable of producing chondroitin obtained according to the method described above to inactivate a gene encoding an enzyme responsible for addition of fructose residues to chondroitin may be used in the culturing step.

According to a preferred embodiment of this invention, a recombinant bacterium obtained from *E. coli* K4 such as *E. coli* DSM23644, is employed as the recombinant microorganism having the ability to directly produce chondroitin.

The method adopted for the cultivation of the bacterium *E. coli* DSM23644 is a general method applicable to the cultivation of members of the genus *Escherichia*. Said method is based on a preferred, but not exclusive, use of a cultivation medium containing per liter:

| | |
|---|---|
| $K_2HPO_4 \cdot 3H_2O$ | 9.7 g |
| $KH_2PO_4$ | 8 g |
| Sodium citrate·$5H_2O$ | 0.5 g |
| $MgCl_2 \cdot 7H_2O$ | 0.2 g |
| Casamino acids | 20 g, |
| $(NH_4)_2SO_4$ | 20 g |
| Glucose | 2 g |
| Yeast extract | 10 g |

Higher levels of chondroitin production can be achieved by suitably modifying the composition of the basal cultivation medium and/or providing further nutrients to the culture by means of substrate feeds.

Culture conditions are selected in order to maximize bacterial growth and chondroitin production. Typically, cultivation is carried out at temperatures between about 25° C. and about 40° C. for about 8 h to about 72 h.

The supernatant is collected preferably by centrifugation and used for the subsequent purification and characterization of the chondroitin produced.

Chondroitin purification was achieved according to an adaptation of the methods described by Rodriguez and Jann (*Eur. J. Biochem.*, Vol. 177, 117-124, FEBS, October 1988).

Briefly summarized, the method adopted to purify chondroitin is based on several steps of precipitation starting from the culture supernatant and a final drying under vacuum.

The identity of the product recovered can be ascertained by a number of methods, preferably by a combination of methods providing evidence of the structure of the polysaccharide chain and of the absence of fructose residues.

The absence of fructose from the purified product can be advantageously verified by means of an acid hydrolysis of the product, in conditions known to release fructose from native K4 polysaccharide, followed by a specific assay for any fructose released as a consequence. This test consistently showed that the polysaccharide recovered from cultures of the bacterium *E. coli* DSM23644 contained no fructose, in contrast with the native K4 polysaccharide obtained from the *Escherichia coli* O5:K4:H4 strain U1-41 that consistently produced a polysaccharide containing fructose in the amounts expected from the structural formula of the K4 polysaccharide.

A further confirmation of the identity of the product recovered from the cultures of the bacterium *E. coli* DSM23644 was obtained by subjecting the product to digestion with the enzyme Chondroitinase ABC, which is known to completely degrade to disaccharides the fructose-free chondroitin polysaccharide, but not the native K4 polysaccharide.

In other words, Chondroitinase ABC is unable to digest the native K4 polysaccharide. Chondroitinase ABC digestion experiments of the product recovered from cultures of the bacterium *E. coli* DSM23644 yielded the amounts of the disaccharide product expected from a complete digestion, thus confirming the nature of the polysaccharide backbone and in particular the absence of fructose residues.

According to one embodiment of the present invention, to confirm the function of kfoE as the gene coding for the K4 fructosyl-transferase activity, a recombinant plasmid carrying wild type kfoE nucleotide sequence has been constructed and introduced into *E. coli* K4 strain (ΔkfoE) to mediate the complementation of lost function.

Briefly, kfoE gene has been amplified and cloned into pTrcHis plasmid (Invitrogen Corporation, 5791 Van Allen Way, PO Box 6482, Carlsbad, Calif.) within NcoI and BamHI restriction sites. The construct pTrcHis-kfoE has been used to transform by electroporation the recombinant *E. coli* (ΔkfoE) and the transformants have been selected at 37° C., on plates containing 100 μg/mL ampicillin.

E. coli (ΔkfoE) transformants carrying the construct pTrcHis-kfoE have been cultured and K4 polysaccharide purified according to Rodriguez and Jann (*Eur. J. Biochem.*, Vol. 177, 117, 117-124, FEBS, October 1988) and in order to quantify the fructose present in the product recovered, free fructose was determined both before and after hydrolysis with 0.2 M trifluoroacetic acid for 1 h at 99° C. Free fructose assayed before and after hydrolysis has been taken as the fructose bound to the starting K4 molecule.

```
OL151:
                                                      (SEQ ID N° 3)
atgcttctaataatgtctggttcctatgttcaacaagaatgtgtaggctggagctgcttc OL152:
                                                      (SEQ ID N° 4)
tcatactgcagcctccttaaaaatttcatataatctaaatgcacatatgaatatcctcct ta.
```

The product recovered from the culture of *E. coli* DSM23644 transformed by pTrcHis-kfoE showed the presence of bound fructose, confirming that in this strain the loss of fructosyl-transferase activity was complemented by plasmid.

a) DNA fragment carrying a kanamycin resistance cassette (kanamycin), flanked by two FRT (Flippase Recognition Targets) recombination sequences; the kanamycin resistance gene is derived from pKD4 plasmid template by using P1 and P2 priming sites;

b) Detailed structure of the K antigen gene cluster of *E. coli* O5:K4:H4 strain U1-41, where kfoD and kfoF are the flanking genes of kfoE;

c) *E. coli* K4 (ΔkfoE/kan$^R$) chromosomal DNA showing the disruption of the kfoE gene by substituting a fragment of original DNA with the kanamycin resistance gene (kanamycin); and d) *E. coli* K4 (ΔkfoE) chromosomal DNA showing the final deletion of most of the kfoE gene.

Figure 2:
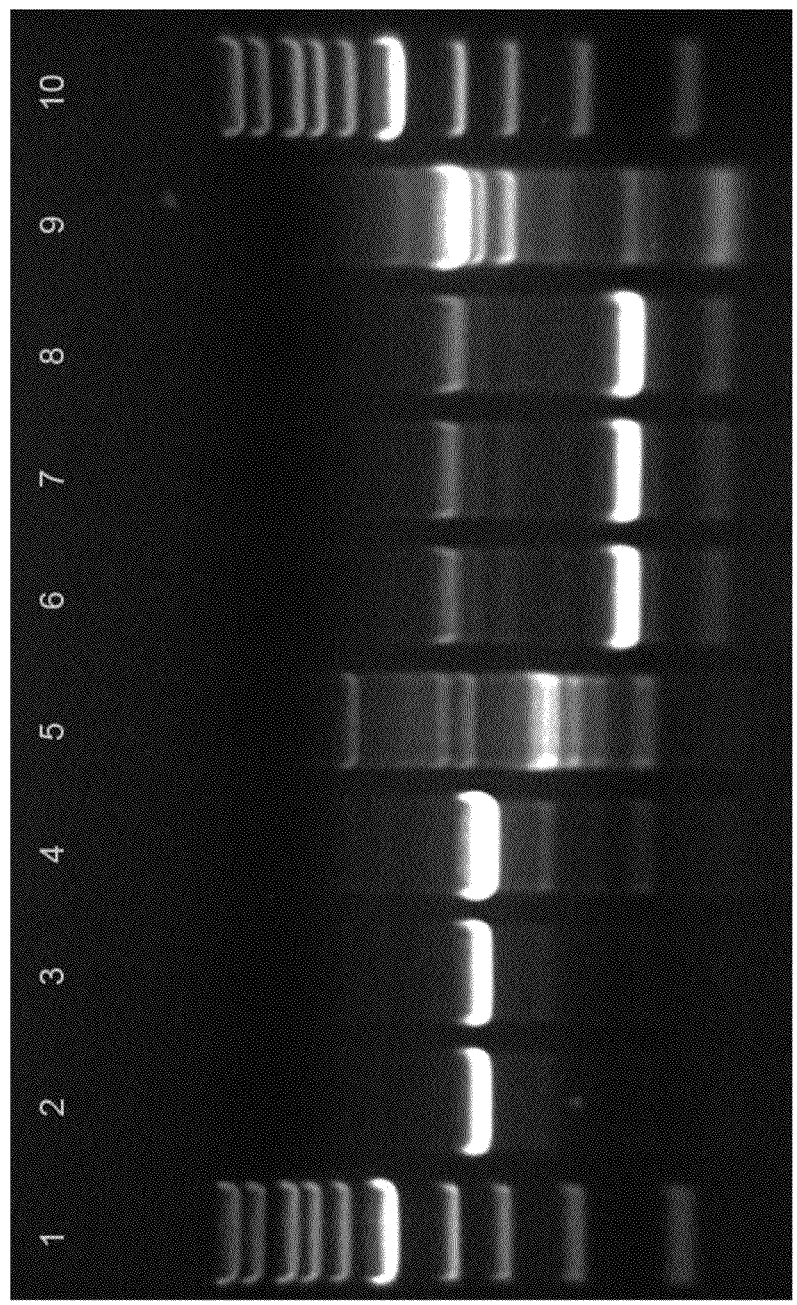

FIG. 2 shows the results of PCR amplification carried out on 3 *E. coli* K4 (ΔkfoE/kan$^R$) transformants to verify the sequence of the 3' and 5' kfoE remaining flanking regions:

lanes 1 and 10 show the molecular weight marker (1 Kb ladder);

lanes 2-4: PCR product of residual kfoE 3' terminus of the 3 transformants;

lanes 6-8: PCR product of residual KfoE 5' terminus of the 3 transformants; and lanes 5 and 9: PCR product of *Escherichia coli* O5:K4:H4 strain U1-41 obtained by using the 3' and 5' pairs of primers respectively.

Figure 3:
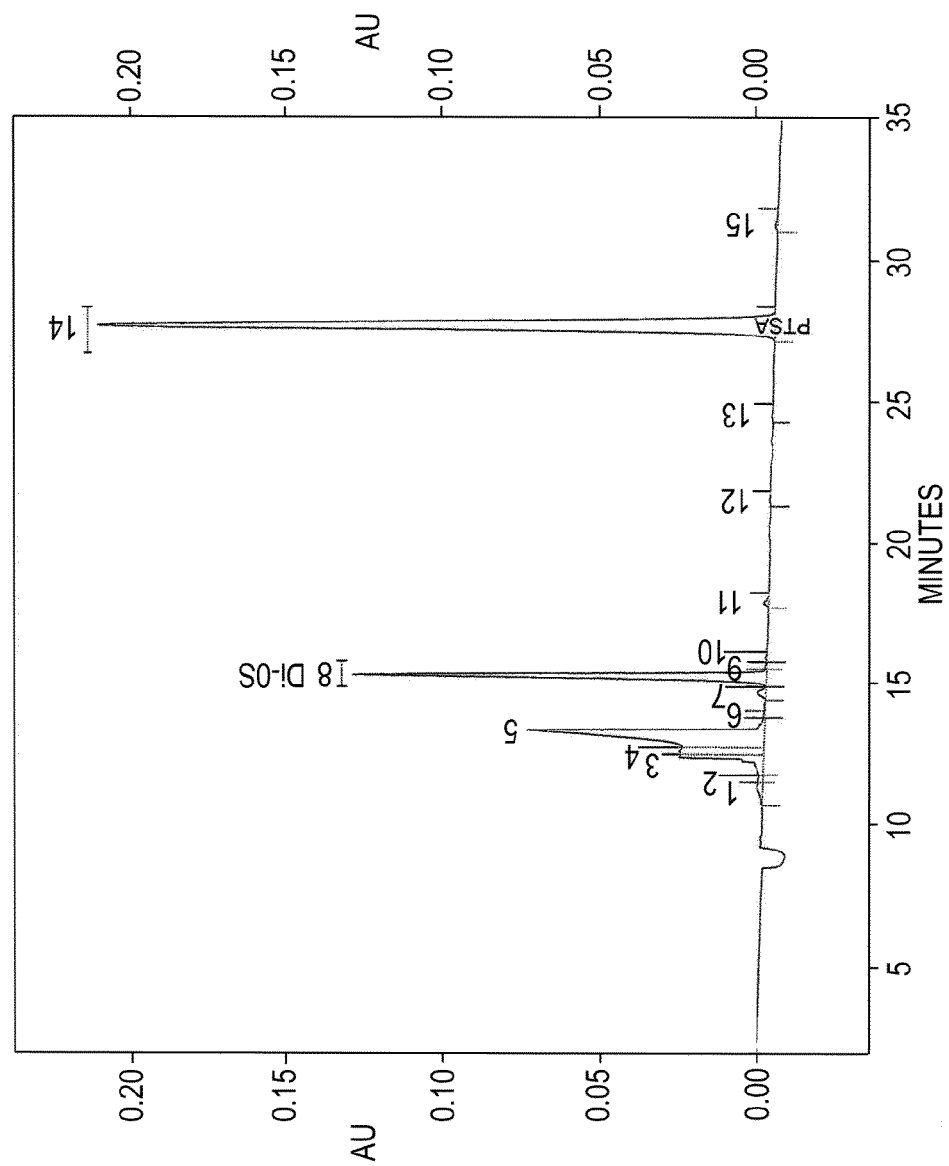

FIG. 3 shows a chromatogram of the polysaccharide produced by *E. coli* DSM23644 analyzed by Capillary Electrophoresis after digestion with Chondroitinase ABC, where the unsaturated Δ-disaccharide (Δdi-0S), typical of chondroitin digestion with Chondroitinase ABC is shown (peak 8).

Figure 4:
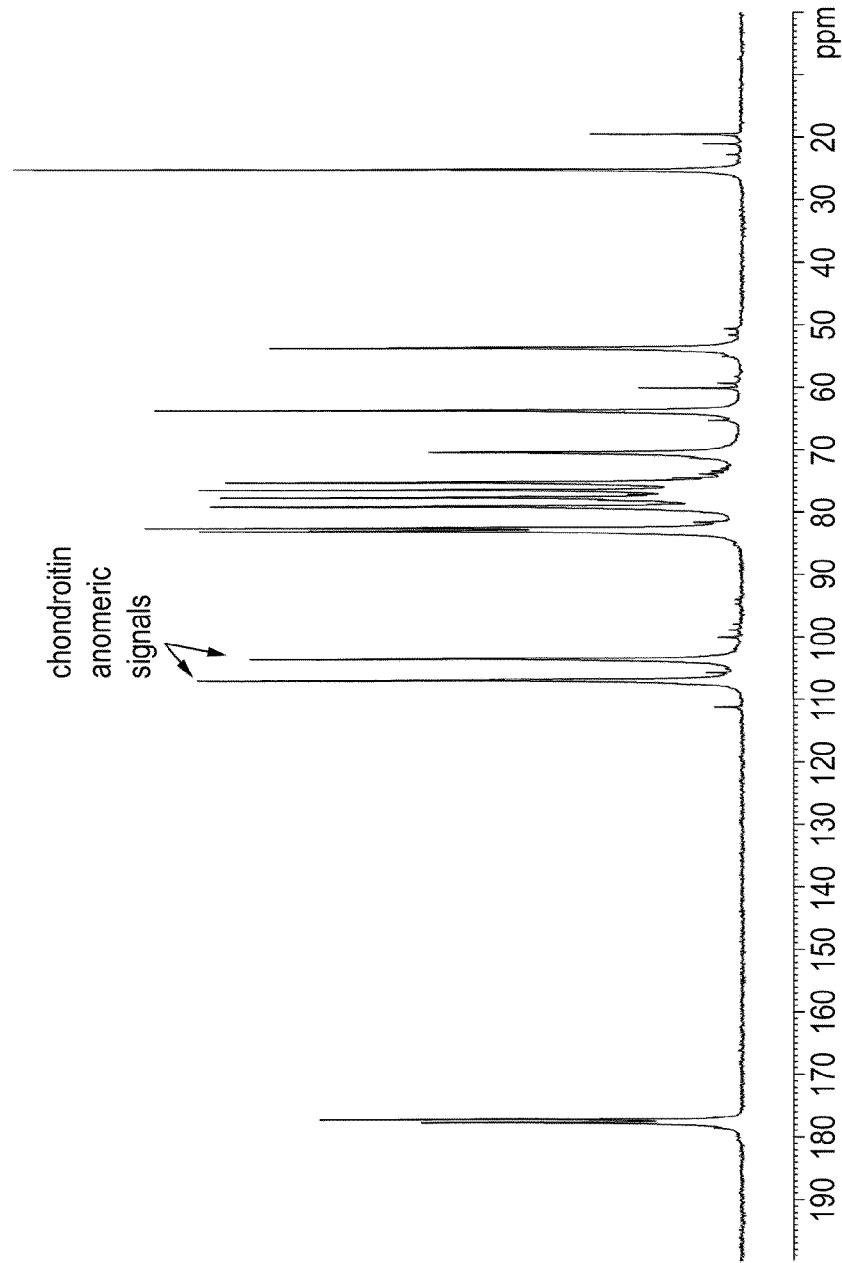

FIG. 4 shows a $^{13}$C-NMR spectrum of the chondroitin produced by *E. coli* DSM23644 obtained according to Example 3.

EXAMPLES

Example 1

Construction of *E. coli* K4 (ΔkfoE/Kan$^R$) Strain

Figure 1:
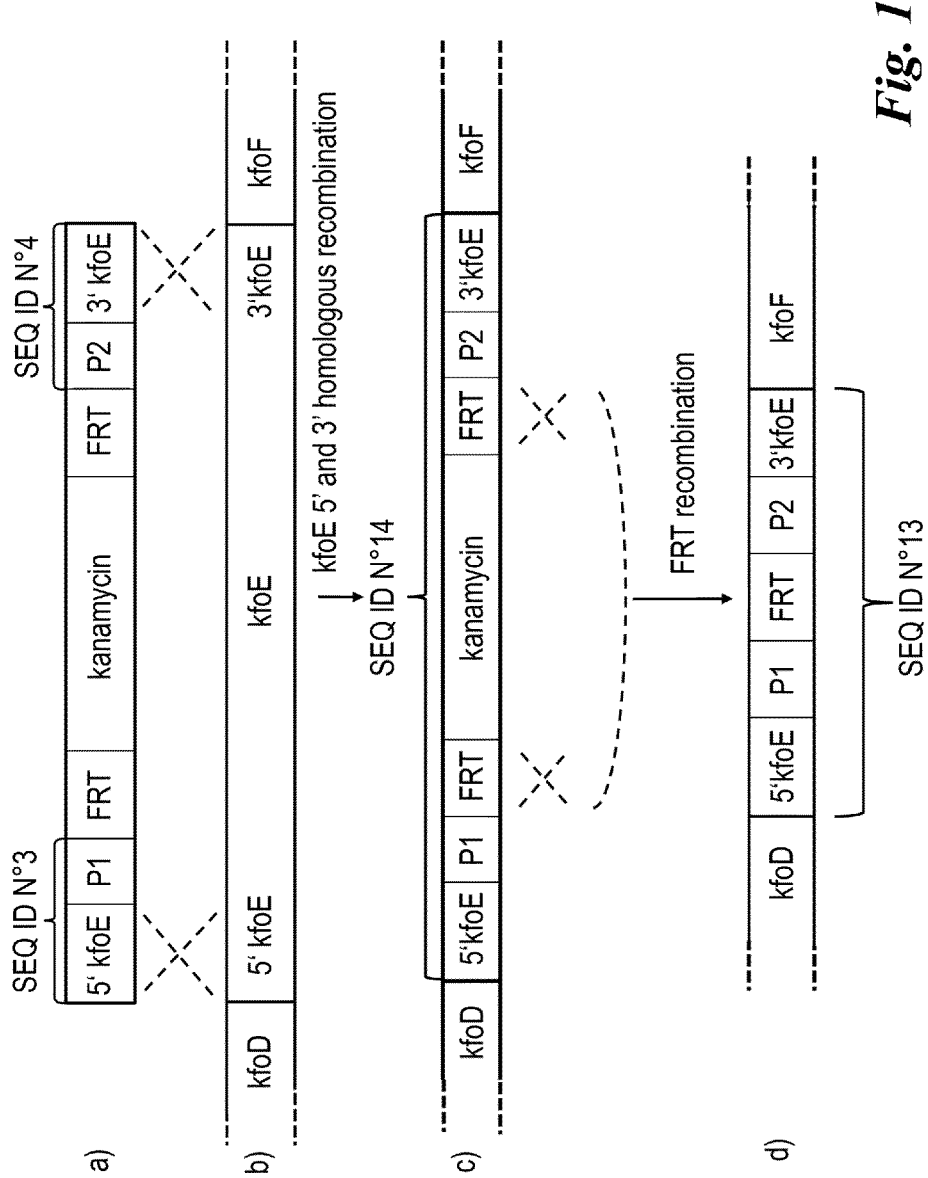
FIG. 1 shows schematically the genetic modifications to which *Escherichia coli* O5:K4:H4 strain U1-41 was subjected resulting in the construction of *E. coli* K4 (ΔkfoE/kan$^R$) and *E. coli* K4 (ΔkfoE)

The construction of the linear DNA fragment (FIG. 1a) carrying both kan$^R$ gene and kfoE homologous termini was achieved by PCR using the pKD4 vector as a template and the following PCR primers:

In each oligonucleotide sequence, the first 40 nucleotides provide kfoE gene homology and the remaining 20 nucleotides provide pKD4 template plasmid homology (P1 and P2 priming sites).

PCR was performed on 120 ng of template DNA according to the following conditions:

94° C.×3 min, (94° C.×1 min, 40° C.×1 min, 68° C.×2 min)×5 cycles, (94° C.×1 min, 59° C.×1 min, 68° C.×2 min)×30 cycles, 68° C.×10 min, 4° C.×10 min.

The PCR product was gel-purified and the bacteria were transformed.

*Escherichia coli* O5:K4:H4 strain U1-41 (FIG. 1b) was prepared and transformed by electroporation with the pKD46 plasmid according to Datsenko and Wanner (*PNAS*, Vol. 97, No 12, 6640-6645, Jun. 6, 2000), which is hereby incorporated by reference in its entirety, then plated onto ampicillin-containing medium.

Ampicillin-resistant transformants were identified and isolated.

Two transformants were verified by plasmid extraction and PCR using the following primers and conditions:

```
OL149:
                                        (SEQ ID N° 5)
ccactcataaatcctcatagag OL150:
                                        (SEQ ID N° 6)
ccaacttacttctgacaacgat
``` at 94° C.×3 min, (94° C.×1 min, 43° C.×1 min, 68° C.×2.5 min)×30 cycles, 68° C.×10 min, 4° C.×10 min.

The PCR product was analyzed by 0.8% agarose gel electophoresis and a product with a size of 1799 base pairs was identified, in complete accordance with the expected product size.

One of the two pKD46 transformants was submitted to a subsequent electroporation, using the DNA fragment carrying both the kanamycin resistance cassette and the kfoE homologous termini.

Plate selection on media containing both ampicillin and kanamycin was used to isolate recombinants carrying the substitution of most of kfoE nucleotide sequence with the kanamycin resistance gene.

Three double transformants were verified by PCR amplification of both kfoE 3' and 5' flanking regions, using the appropriate following primers:

```
OL153:
                                              (SEQ ID N° 7)
    aatccgacggggactgtagatt OL142:
                                              (SEQ ID N° 8)
    aactgttcgccaggctcaag OL143:
                                              (SEQ ID N° 9)
    gcgttttcccttgtccagat OL154:
                                              (SEQ ID N° 10)
    gctaatgtatatgattgccaggt
``` at 95° C.×5 min, (94° C.×1 min, 47° C.×1 min, 68° C.×2 min)×30 cycles, 68° C.×10 min, 4° C.×10 min.

PCR products were analyzed by 0.8% agarose gel electrophoresis and two products with a size of 1773 base pairs for 3' terminus amplification and 769 base pairs for 5' terminus amplification of kfoE gene respectively were identified, in complete accord with the expected products size (FIG. 2).

In order to verify the orientation of the kanamycin resistance gene and to ensure the correct direction of gene transcription, a further analysis of transformants was carried out by sequencing analysis of E. coli K4 (ΔkfoE/kan$^R$) (FIG. 1c), using the following oligonucleotides:

```
OL153:
                                              (SEQ ID N° 7)
    aatccgacggggactgtagatt OL154:
                                              (SEQ ID N° 10)
    gctaatgtatatgattgccaggt
```

The resulting nucleotide sequence is identified by SEQ ID No 14.

Example 2

Construction of E. coli K4 (ΔkfoE) Strain

In order to obtain the E. coli K4 strain (ΔkfoE) lacking the kanamycin resistance cassette and carrying a deletion of most of the kfoE gene with the attendant loss of function, a further transformation of E. coli K4 strain (ΔkfoE/kan$^R$) with the pCP20 plasmid was performed.

After the electroporation step, the transformants were selected on media containing ampicillin at 30° C. and then colony purified.

Putative transformants were grown on non-selective plates at 43° C. and then tested for loss of all antibiotic resistances.

E. coli K4 strain (ΔkfoE) transformants were verified by sequencing of both kfoE flanking 3' and 5' remaining termini (FIG. 1d), using the following oligonucleotides:

```
                                              (SEQ ID N° 11)
    OL169:
        tgaggtgattgttggtaaaccttggtg (SEQ ID N° 12)
    OL166:
        tactgtttctgcttgccccgagtt
```

The resulting nucleotide sequence is identified by SEQ ID No 13

Example 3

Cultivation of E. coli DSM23644 and Chondroitin Analysis

Cultivation of E. coli DSM23644 was carried out according to Rodriguez and Jann (Eur. J. Biochem., Vol. 177, 117-124, FEBS, October 1988), which is hereby incorporated by reference in its entirety.

Briefly, vegetative stage of culture was realized starting from 0.5 ml of thawed culture stock, inoculating a flask containing 20 ml of broth culture consisting per liter of:

| | |
|---|---|
| $K_2HPO_4 \cdot 3H_2O$ | 9.7 g |
| $KH_2PO_4$ | 8 g |
| Sodium citrate·$5H_2O$ | 0.5 g |
| $MgCl_2 \cdot 7H_2O$ | 0.2 g |
| Casamino acids | 20 g |
| $(NH_4)_2SO_4$ | 20 g |
| Glucose | 2 g |
| Yeast extract | 10 g | incubated at 37° C. for 16 h, with shaking at 180 rpm and 2.5 cm of displacement.

The subsequent cultivation stage was carried out in batch culture, in a 500 ml-baffled flask containing 85 ml of broth culture as described above, inoculated with 0.05% of vegetative culture prepared as described above and incubated at 37° C. for 48 h with shaking at 180 rpm and 2.5 cm of displacement.

At the end of the incubation the culture was harvested by centrifugation and the supernatant was subjected to purification in order to isolate and characterize the produced chondroitin.

Chondroitin purification was achieved according to an adaptation of the methods described by Rodriguez and Jann (Eur. J. Biochem., Vol. 177, 117-124, FEBS, October 1988).

Briefly, the polysaccharide was precipitated from the culture supernatant by Cetavlon (alkyl-trimethylammonium bromide, CAS No 7192-88-3), extracted with 0.5M NaOH at 3° C., neutralized and subsequently purified by 3 cycles of precipitation with 80% ethanol.

A final step of purification was carried out with 90% cold phenol pH 6.8 to precipitate contaminating proteins thus recovering the aqueous phase by centrifugation. The purified chondroitin was recovered from the aqueous phase by precipitation with 80% ethanol and drying under vacuum.

Several analytical approaches were used to ascertain the nature of the chondroitin produced.

The first approach was based on the presence or absence of fructose in the product recovered from the culture after acid hydrolysis carried out with 0.2M trifluoroacetic acid for 1 h at 99° C.

In order to quantify the fructose present in the product recovered, free fructose was determined both before and after hydrolysis. Fructose was assayed enzymatically using the EnzyPlus Sucrose/D-Glucose/D-Fructose kit supplied by BIOCONTROL (BioControl Systems Inc., 12822 SE 32nd Street, Bellevue, Wash. 98005, United States).

The difference between the free fructose present after hydrolysis and that present before hydrolysis was taken as the fructose bound to the starting K4 molecule.

The product recovered from the culture of E. coli DSM23644 showed no presence of bound fructose, confirming that this strain produces a fructose-free polysaccharide.

The absence of bound fructose from the polysaccharide recovered from cultures of E. coli DSM23644 as described above was confirmed by enzyme digestion with Chondroitinase ABC. It was further demonstrated that the purified chondroitin when digested with Chondroitinase ABC yielded the unsaturated Δ-disaccharide (Δdi-0S) typical of chondroitin digestion as confirmed by Capillary Electrophoresis (CE), using the Micellar Electrokinetic Chromatography (MECK) technique (FIG. 3).

The confirmation of the Δdi-0S structure was obtained by the use of the appropriate Δ-disaccharide reference standard (equivalent electrophoretic elution).

The quantitative determination of the Δdi-0S obtained was achieved by means of an external calibration curve.

Finally, the purified chondroitin polysaccharide produced by E. coli DSM23644 was characterized by $C^{13}$ NMR (FIG. 4).

This technique showed that the product in question was spectrally identical with the product obtained after the removal of fructose from the native K4 polysaccharide by acid hydrolysis.

Example 4

Plasmid-Mediated Complementation of kfoE Function

In order to verify the function of kfoE as the gene coding for the K4 fructosyl-transferase activity, a recombinant plasmid carrying wild type kfoE nucleotide sequence was constructed and introduced into E. coli K4 strain (ΔkfoE) to mediate the complementation of lost function.

kfoE gene was amplified by using the following oligonucleotides:

```
OL172:
                                           (SEQ ID N° 15)
acaacatgttactaataatgtctggttcctatgttc OL173:
                                           (SEQ ID N° 16)
actggatccttatcatactgcagcctcctta
```

The pTrcHis plasmid (4400 bp—Invitrogen Corporation, 5791 Van Allen Way, PO Box 6482, Carlsbad, Calif.) was used to introduce the amplified and gel-purified kfoE gene (1569 bp) into suitable cloning sites.

70 ng of pTrcHis vector digested by NcoI and BamHI restriction enzymes and 75 ng of kfoE gene having compatible PciI/BamHI digested ends were subjected to a ligation reaction at 25° C. for 15 min.

Then 50 μL of Escherichia coli DH5α competent cells (Invitrogen Corporation, 5791 Van Allen Way, PO Box 6482, Carlsbad, Calif.) were electroporated with 5 μL of ligation mixture and five transformants were selected at 37° C., on plates containing 100 μg/mL ampicillin.

After colony purification, the constructed plasmid pTrcHis-kfoE was extracted and digested by Mfe I restriction enzyme, which was able to cut the DNA construct within the inserted kfoE sequence.

By means of gel electrophoresis analysis, 3 of 5 transformants after Mfe I digestion showed the expected length of 5887 bp and the sequences analysis confirmed the correct insertion of kfoE gene.

The verified pTrcHis-kfoE construct was used to transform by electroporation the recombinant E. coli DSM23644 and transformants were selected on plates containing 100 μg/mL ampicillin.

Selected transformants were cultured according to the conditions described in Example 3 and K4 polysaccharide was purified according to Rodriguez and Jann (Eur. J. Biochem., Vol. 177, 117-124, FEBS, October 1988).

In order to quantify the fructose present in the product recovered, free fructose was determined both before and after hydrolysis with 0.2 M trifluoroacetic acid for 1 h at 99° C. Fructose was assayed enzymatically using the EnzyPlus Sucrose/D-Glucose/D-Fructose kit.

The difference between the free fructose present after hydrolysis and that present before hydrolysis was taken as the fructose bound to the starting K4 molecule.

The product recovered from the culture of E. coli DSM23644 transformed by pTrcHis-kfoE showed the presence of bound fructose, confirming that in this strain the loss of fructosyl-transferase activity was complemented by plasmid.

The invention claimed is:

1. A method for biotechnological production of chondroitin, comprising the following steps:
   a) cultivating in a suitable medium a recombinant microorganism producing chondroitin, defined as a linear glycosaminoglycan constituted by alternating residues of D-glucuronic acid (GlcUA) and N-acetyl-D-galactosamine (GalNAc) bound by β1-3 (GlcUA→GalNAc) and β1-4 (GalNAc→GlcUA) bonds, characterized in that in said microorganism the kfoE gene originally present which encodes an enzyme responsible for the addition of fructose residues to the linear chondroitin backbone is inactivated by deletion or substitution entirely or in part of said gene or disruption by insertion of an additional nucleotide sequence, and wherein the kfoE gene encodes a protein comprising the amino acid sequence of SEQ ID No 2; and
   b) recovering and purifying the chondroitin present in the microbial culture.

2. The method according to claim 1 wherein the kfoE gene comprises a DNA comprising the nucleotide sequence of SEQ ID No 1.

3. The method according to claim 1 wherein the kfoE gene is inactivated by entire or partial substitution thereof with a kanamycin resistance cassette and its subsequent removal, resulting in the entire or partial deletion of the kfoE gene.

4. The method according to claim 2 wherein the kfoE gene is inactivated by entire or partial substitution thereof with a kanamycin resistance cassette and its subsequent removal, resulting in the entire or partial deletion of the kfoE gene.

5. The method according to claim 1, wherein the recombinant microorganism is derived from a bacterium belonging to a genus selected from *Escherichia, Haemophilus, Campylobacter, Gloeocapsa*, and *Vibrio*.

6. The method according to claim 2, wherein the recombinant microorganism is derived from a bacterium belonging to a genus selected from *Escherichia, Haemophilus, Campylobacter, Gloeocapsa*, and *Vibrio*.

7. The method according to claim 1 wherein the recombinant microorganism is *Escherichia coli* DSM23644 or *Escherichia coli* DSM23578.

8. The method according to claim 7 wherein the recombinant microorganism is *Escherichia coli* DSM23644.

9. The method according to claim 2 wherein the recombinant microorganism is *Escherichia coli* DSM23644 or *Escherichia coli* DSM23578.

10. The method according to claim 9 wherein the recombinant microorganism is *Escherichia coli* DSM23644.

* * * * *

SEQUENCE LISTING

```
<160> NUMBER OF SEQ ID NOS: 16

<210> SEQ ID NO 1
<211> LENGTH: 1566
<212> TYPE: DNA
<213> ORGANISM: Escherichia coli
<220> FEATURE:
<221> NAME/KEY: gene
<222> LOCATION: (1)..(1566)

<400> SEQUENCE: 1
atgcttctaa taatgtctgg ttcctatgtt caacaagaat tagggccga  atttggttct      60 attcctccaa gctttcttcc tttagctaat aaacgattat ttaagcatca  agtatcttta     120
gggcatgatg gtcatgcaat atatctggtt ttaccggaag attttgtgtt  tgacaaacat     180
gattatgaat ggttgcttcg taataaagta acaatgatcc ctgtcgatag  taacttgaca     240
ttagggcaag cgatagttac cgcatggaat ttaataggag ataaagatga  caaaggctta     300
caattattgt ttggcgatac actctttaaa aaaattcctg caggggagga  attagtagca     360
aaaagtcatc ctgatgaaaa ttatcaatgg gccatttttt acgaaacaga  gttaagagcc     420
```

-continued

```
gtcagtagag aagataataa aaatgtaatt tgtgggtatt tttcttttag aaaaccgaat    480
ttttttatta gggaattagt tacttcaaaa tttgatttta cggcggcact taaaaagtat    540
cacgacagct atagtttagc ctctatatac gtgtctgatt ggcttgattt tggacatatt    600
aatacatact ataagtcaaa agtacaatac acaacccagc gtgcatttaa tgaattatgc    660
attacaacaa atccgttat  caaatcaagt tcaaatgaaa gtaaaattga agctgaatca    720
aaatggtttg aaactattcc cggagaatta aagatctata ctccaatgtt attggaaccg    780
tttgatcata tcagaaagag ttataagctt gaatatttat ataatacgac gttaaatgaa    840
ttatttgttt tttctcgcct accaaataat attttaacaa atatattaat aagttgttta    900
gacttcatcg atctgtgcaa agaatatcat tcaattgata ctgacaaaaa tatactgcaa    960
gatttatttt atgaaaaaac gattgagcgg gttagcaagt acataacaga tttaaatatt   1020
gatccaaatg caaatggaa  ttttaataat aatataagcg tttcaattaa tgatattctt   1080
tatgatacta taaatttat  cccaagtgaa ctgcaatata aaactattat gcatggcgat   1140
ttatgcttta gtaatataat ttttaacttt agaactggta gaatacaagt ttttgatccc   1200
agaggattga accactctgg agaaataagt atttatggtg attttcgtta tgatatagct   1260
aaattatcac attcaatact agggctctat gattggataa ttgcaggata ttatataata   1320
aataaaaaaa ataaaactca tagtattgaa ttcaaaatta atattgataa taaattgttt   1380
gaaattcaat caacatttgt ttctataata aaagagaaat attcaatctc cgaaaaatca   1440
ttgtatgcga tgcaaataca tttattttta tcaatgcttc cccttcattc cgatgacaaa   1500
aaaaggcaag atgcactatt tgctaatgca tttagattat atgaaatttt taaggaggct   1560
gcagta                                                              1566
```

<210> SEQ ID NO 2
<211> LENGTH: 522
<212> TYPE: PRT
<213> ORGANISM: Escherichia coli
<220> FEATURE:
<221> NAME/KEY: protein
<222> LOCATION: (1)..(522)

<400> SEQUENCE: 2

```
Met Leu Leu Ile Met Ser Gly Ser Tyr Val Gln Gln Glu Leu Gly Ala
1               5                   10                  15

Glu Phe Gly Ser Ile Pro Pro Ser Phe Leu Pro Leu Ala Asn Lys Arg
            20                  25                  30

Leu Phe Lys His Gln Val Ser Leu Gly His Asp Gly His Ala Ile Tyr
        35                  40                  45

Leu Val Leu Pro Glu Asp Phe Val Phe Asp Lys His Asp Tyr Glu Trp
    50                  55                  60

Leu Leu Arg Asn Lys Val Thr Met Ile Pro Val Asp Ser Asn Leu Thr
65                  70                  75                  80

Leu Gly Gln Ala Ile Val Thr Ala Trp Asn Leu Ile Gly Asp Lys Asp
                85                  90                  95

Asp Lys Gly Leu Gln Leu Leu Phe Gly Asp Thr Leu Phe Lys Lys Ile
            100                 105                 110

Pro Ala Gly Glu Glu Leu Val Ala Lys Ser His Pro Asp Glu Asn Tyr
        115                 120                 125

Gln Trp Ala Ile Phe Tyr Glu Thr Glu Leu Arg Ala Val Ser Arg Glu
    130                 135                 140

Asp Asn Lys Asn Val Ile Cys Gly Tyr Phe Ser Phe Arg Lys Pro Asn
```

```
              145                 150                 155                 160
        Phe Phe Ile Arg Glu Leu Val Thr Ser Lys Phe Asp Phe Thr Ala Ala
                        165                 170                 175
        Leu Lys Lys Tyr His Asp Ser Tyr Ser Leu Ala Ser Ile Tyr Val Ser
                        180                 185                 190
        Asp Trp Leu Asp Phe Gly His Ile Asn Thr Tyr Tyr Lys Ser Lys Val
                        195                 200                 205
        Gln Tyr Thr Thr Gln Arg Ala Phe Asn Glu Leu Cys Ile Thr Thr Lys
                        210                 215                 220
        Ser Val Ile Lys Ser Ser Asn Glu Ser Lys Ile Glu Ala Glu Ser
        225                 230                 235                 240
        Lys Trp Phe Glu Thr Ile Pro Gly Glu Leu Lys Ile Tyr Thr Pro Met
                        245                 250                 255
        Leu Leu Glu Pro Phe Asp His Ile Arg Lys Ser Tyr Lys Leu Glu Tyr
                        260                 265                 270
        Leu Tyr Asn Thr Thr Leu Asn Glu Leu Phe Val Phe Ser Arg Leu Pro
                        275                 280                 285
        Asn Asn Ile Leu Thr Asn Ile Leu Ile Ser Cys Leu Asp Phe Ile Asp
        290                 295                 300
        Leu Cys Lys Glu Tyr His Ser Ile Asp Thr Asp Lys Asn Ile Leu Gln
        305                 310                 315                 320
        Asp Leu Phe Tyr Glu Lys Thr Ile Glu Arg Val Ser Lys Tyr Ile Thr
                        325                 330                 335
        Asp Leu Asn Ile Asp Pro Asn Ala Lys Trp Asn Phe Asn Asn Asn Ile
                        340                 345                 350
        Ser Val Ser Ile Asn Asp Ile Leu Tyr Asp Thr Asn Lys Phe Ile Pro
                        355                 360                 365
        Ser Glu Leu Gln Tyr Lys Thr Ile Met His Gly Asp Leu Cys Phe Ser
                        370                 375                 380
        Asn Ile Ile Phe Asn Phe Arg Thr Gly Arg Ile Gln Val Phe Asp Pro
        385                 390                 395                 400
        Arg Gly Leu Asn His Ser Gly Glu Ile Ser Ile Tyr Gly Asp Phe Arg
                        405                 410                 415
        Tyr Asp Ile Ala Lys Leu Ser His Ser Ile Leu Gly Leu Tyr Asp Trp
                        420                 425                 430
        Ile Ile Ala Gly Tyr Tyr Ile Ile Asn Lys Lys Asn Lys Thr His Ser
                        435                 440                 445
        Ile Glu Phe Lys Ile Asn Ile Asp Asn Lys Leu Phe Glu Ile Gln Ser
                        450                 455                 460
        Thr Phe Val Ser Ile Ile Lys Glu Lys Tyr Ser Ile Ser Glu Lys Ser
        465                 470                 475                 480
        Leu Tyr Ala Met Gln Ile His Leu Phe Leu Ser Met Leu Pro Leu His
                        485                 490                 495
        Ser Asp Asp Lys Lys Arg Gln Asp Ala Leu Phe Ala Asn Ala Phe Arg
                        500                 505                 510
        Leu Tyr Glu Ile Phe Lys Glu Ala Ala Val
                        515                 520

<210> SEQ ID NO 3
<211> LENGTH: 60
<212> TYPE: DNA
<213> ORGANISM: artificial sequence
<220> FEATURE:
<223> OTHER INFORMATION: OL151
<220> FEATURE:
```

-continued

<221> NAME/KEY: oligonucleotide
<222> LOCATION: (1)..(60)

<400> SEQUENCE: 3
atgcttctaa taatgtctgg ttcctatgtt caacaagaat gtgtaggctg gagctgcttc    60

<210> SEQ ID NO 4
<211> LENGTH: 62
<212> TYPE: DNA
<213> ORGANISM: artificial sequence
<220> FEATURE:
<223> OTHER INFORMATION: OL152
<220> FEATURE:
<221> NAME/KEY: oligonucleotide
<222> LOCATION: (1)..(62)

<400> SEQUENCE: 4
tcatactgca gcctccttaa aaatttcata taatctaaat gcacatatga atatcctcct    60
ta    62

<210> SEQ ID NO 5
<211> LENGTH: 22
<212> TYPE: DNA
<213> ORGANISM: artificial sequence
<220> FEATURE:
<223> OTHER INFORMATION: OL149
<220> FEATURE:
<221> NAME/KEY: oligonucleotide
<222> LOCATION: (1)..(22)

<400> SEQUENCE: 5
ccactcataa atcctcatag ag    22

<210> SEQ ID NO 6
<211> LENGTH: 22
<212> TYPE: DNA
<213> ORGANISM: artificial sequence
<220> FEATURE:
<223> OTHER INFORMATION: OL150
<220> FEATURE:
<221> NAME/KEY: oligonucleotide
<222> LOCATION: (1)..(22)

<400> SEQUENCE: 6
ccaacttact tctgacaacg at    22

<210> SEQ ID NO 7
<211> LENGTH: 22
<212> TYPE: DNA
<213> ORGANISM: artificial sequence
<220> FEATURE:
<223> OTHER INFORMATION: OL153
<220> FEATURE:
<221> NAME/KEY: oligonucleotide
<222> LOCATION: (1)..(22)

<400> SEQUENCE: 7
aatccgacgg ggactgtaga tt    22

<210> SEQ ID NO 8
<211> LENGTH: 20
<212> TYPE: DNA
<213> ORGANISM: artificial sequence
<220> FEATURE:
<223> OTHER INFORMATION: OL142
<220> FEATURE:
<221> NAME/KEY: oligonucleotide
<222> LOCATION: (1)..(20)

```
<400> SEQUENCE: 8
aactgttcgc caggctcaag                                                    20

<210> SEQ ID NO 9
<211> LENGTH: 20
<212> TYPE: DNA
<213> ORGANISM: artificial sequence
<220> FEATURE:
<223> OTHER INFORMATION: OL143
<220> FEATURE:
<221> NAME/KEY: oligonucleotide
<222> LOCATION: (1)..(20)

<400> SEQUENCE: 9
gcgttttccc ttgtccagat                                                    20

<210> SEQ ID NO 10
<211> LENGTH: 23
<212> TYPE: DNA
<213> ORGANISM: artificial sequence
<220> FEATURE:
<223> OTHER INFORMATION: OL154
<220> FEATURE:
<221> NAME/KEY: oligonucleotide
<222> LOCATION: (1)..(23)

<400> SEQUENCE: 10
gctaatgtat atgattgcca ggt                                                23

<210> SEQ ID NO 11
<211> LENGTH: 27
<212> TYPE: DNA
<213> ORGANISM: artificial sequence
<220> FEATURE:
<223> OTHER INFORMATION: OL169
<220> FEATURE:
<221> NAME/KEY: oligonucleotide
<222> LOCATION: (1)..(27)

<400> SEQUENCE: 11
tgaggtgatt gttggtaaac cttggtg                                            27

<210> SEQ ID NO 12
<211> LENGTH: 25
<212> TYPE: DNA
<213> ORGANISM: artificial sequence
<220> FEATURE:
<223> OTHER INFORMATION: OL166
<220> FEATURE:
<221> NAME/KEY: oligonucleotide
<222> LOCATION: (1)..(25)

<400> SEQUENCE: 12
tactgtttct gcttgccccc gagtt                                              25

<210> SEQ ID NO 13
<211> LENGTH: 167
<212> TYPE: DNA
<213> ORGANISM: Escherichia coli
<220> FEATURE:
<221> NAME/KEY: gene
<222> LOCATION: (1)..(167)
<223> OTHER INFORMATION: rearranged

<400> SEQUENCE: 13
atgcttctaa taatgtctgg ttcctatgtt caacaagaat gtgtaggctg gagctgcttc        60
```

```
gaagttccta tactttctag agaataggaa cttcggaata ggaactaagg aggatattca      120
tatgtgcatt tagattatat gaaattttta aggaggctgc agtatga                    167
```

<210> SEQ ID NO 14
<211> LENGTH: 1559
<212> TYPE: DNA
<213> ORGANISM: Escherichia coli
<220> FEATURE:
<221> NAME/KEY: gene
<222> LOCATION: (1)..(1559)
<223> OTHER INFORMATION: rearranged

<400> SEQUENCE: 14

```
atgcttctaa taatgtctgg ttcctatgtt caacaagaat gtgtaggctg gagctgcttc       60
gaagttccta tactttctag agaataggaa cttcggaata ggaacttcaa gatcccccac      120
gctgccgcaa gcactcaggg cgcaagggct gctaaaggaa gcggaacacg tagaaagcca      180
gtccgcagaa acgtgctgga ccccggatga atgtcagcta ctgggctatc tggacaaggg      240
aaaacgcaag cgcaaagaga aagcaggtag cttgcagtgg gcttacatgg cgatagctag      300
actgggcggt tttatggaca gcaagcgaac cggaattgcc agctggggcg ccctctggta      360
aggttgggaa gccctgcaaa gtaaactgga tggcttttctt gccgccaagg atctgatggc      420 gcagggatc aagatctgat caagagacag gatgaggatc gtttcgcatg attgaacaag       480
atggattgca cgcaggttct ccggccgctt gggtggagag gctattcggc tatgactggg      540
cacaacagac aatcggctgc tctaatgccg ccgtgttccg gctgtcagcg caggggcgcc      600
cggttctttt tgtcaagacc gacctgtccg gtgccctgaa tgaactgcag gacgaggcag      660
cgcggctatc gtggctggcc acgacgggcg ttccttgcgc agctgtgctc gacgttgtca      720
ctgaagcggg aagggactgg ctgctattgg gcgaagtgcc ggggcaggat ctcctgtcat      780
ctcaccttgc tcctgccgag aaagtatcca tcatggctga tgcaatgcgg cggctgcata      840
cgcttgatcc ggctacctgc ccattcgacc accaagcgaa acatcgcatc gagcgagcac      900
gtactcggat ggaagccggt cttgtcgatc aggatgatct ggacgaagag catcaggggc      960
tcgcgccagc cgaactgttc gccaggctca aggcgcgcat gcccgacggc gaggatctcg     1020
tcgtgaccca tggcgatgcc tgcttgccga atatcatggt ggaaaatggc cgcttttctg     1080
gattcatcga ctgtggccgg ctgggtgtgg cggaccgcta tcaggacata gcgttggcta     1140
cccgtgatat tgctgaagag cttggcggcg aatgggctga ccgcttcctc gtgctttacg     1200
gtatcgccgc tcccgattcg cagcgcatcg ccttctatcg ccttcttgac gagttcttct     1260
gagcgggact ctggggttcg aaatgaccga ccaagcgacg cccaacctgc catcacgaga     1320
tttcgattcc accgccgcct tctatgaaag gttgggcttc ggaatcgttt tccgggacgc     1380
cggctggatg atcctccagc gcggggatct catgctggag ttcttcgccc accccagctt     1440
caaaagcgct ctgaagttcc tatactttct agagaatagg aacttcggaa taggaactaa     1500
ggaggatatt catatgtgca tttagattat atgaaatttt taaggaggct gcagtatga      1559
```

<210> SEQ ID NO 15
<211> LENGTH: 36
<212> TYPE: DNA
<213> ORGANISM: artificial sequence
<220> FEATURE:
<223> OTHER INFORMATION: OL172
<220> FEATURE:
<221> NAME/KEY: oligonucleotide
<222> LOCATION: (1)..(36)

```
<400> SEQUENCE: 15
acaacatgtt actaataatg tctggttcct atgttc                              36

<210> SEQ ID NO 16
<211> LENGTH: 31
<212> TYPE: DNA
<213> ORGANISM: artificial sequence
<220> FEATURE:
<223> OTHER INFORMATION: OL173
<220> FEATURE:
<221> NAME/KEY: oligonucleotide
<222> LOCATION: (1)..(31)

<400> SEQUENCE: 16
actggatcct tatcatactg cagcctcctt a                                    31
```